United States Patent
Hershberger

(10) Patent No.: US 7,854,769 B2
(45) Date of Patent: Dec. 21, 2010

(54) METHOD AND INSTRUMENTATION FOR PERFORMING MINIMALLY INVASIVE HIP ARTHROPLASTY

(75) Inventor: Troy W. Hershberger, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1590 days.

(21) Appl. No.: 11/031,197

(22) Filed: Jan. 5, 2005

(65) Prior Publication Data
US 2005/0234470 A1 Oct. 20, 2005

Related U.S. Application Data

(60) Provisional application No. 60/534,270, filed on Jan. 5, 2004.

(51) Int. Cl.
*A61F 2/32* (2006.01)
(52) U.S. Cl. .................... 623/22.42; 623/22.43
(58) Field of Classification Search .............. 623/18.11, 623/20.35, 20.36, 22.11–22.12, 22.4, 22.41–22.47, 623/23.11, 23.15–23.39, 908
See application file for complete search history.

(56) References Cited

U.S. PATENT DOCUMENTS

| 105,044 | A | 7/1870 | Clark |
|---|---|---|---|
| 152,776 | A | 7/1874 | Stockwell |
| 991,566 | A | 5/1911 | Vernaz |
| 1,178,310 | A | 4/1916 | Getaz |
| 4,306,550 | A | 12/1981 | Forte |
| 4,466,429 | A | 8/1984 | Loscher et al. |
| 4,473,070 | A | 9/1984 | Matthews et al. |
| 4,549,319 | A | 10/1985 | Meyer |
| 4,601,289 | A | 7/1986 | Chiarizzio et al. |
| 4,706,659 | A | 11/1987 | Matthews et al. |
| 4,739,750 | A | 4/1988 | Masse et al. |
| 4,765,328 | A | 8/1988 | Keller et al. |
| 4,846,839 | A | 7/1989 | Noiles |
| 4,878,917 | A | 11/1989 | Kranz et al. |
| 4,921,493 | A | 5/1990 | Webb, Jr. et al. |
| 4,938,773 | A | 7/1990 | Strand |

(Continued)

FOREIGN PATENT DOCUMENTS

| DE | 03801678 C1 | 8/1989 |
|---|---|---|
| DE | 04116507 C1 | 9/1992 |
| EP | 898100342 | 9/1989 |

OTHER PUBLICATIONS

Berger, "Total Hip Arthroplasty Using the Minimally Invasive Two-Incision Approach," *Clinical Orthopaedics and Related Research*, vol. 417, 2003, pp. 232-241.

(Continued)

*Primary Examiner*—Todd E Manahan
*Assistant Examiner*—Lynnsy Schneider
(74) *Attorney, Agent, or Firm*—William F. Bahret

(57) ABSTRACT

A method of implanting a modular hip stem implant having a stem portion and a body portion into a medullary canal of a patient's femur utilizing a two-incision technique. The stem portion is inserted through an anterior incision and the body portion is inserted through a posterior incision where they are interconnected in vivo. The modular hip stem implant is then driven into the medullary canal with force applied through either of the two incisions.

16 Claims, 5 Drawing Sheets

U.S. PATENT DOCUMENTS

| | | | |
|---|---|---|---|
| 5,006,121 A | 4/1991 | Hafeli | |
| 5,089,003 A | 2/1992 | Fallin et al. | |
| 5,108,437 A | 4/1992 | Kenna | |
| 5,169,402 A | 12/1992 | Elloy | |
| 5,190,550 A | 3/1993 | Miller et al. | |
| 5,203,595 A | 4/1993 | Borzone et al. | |
| 5,342,366 A | 8/1994 | Whiteside et al. | |
| 5,441,501 A | 8/1995 | Kenyon | |
| 5,443,471 A | 8/1995 | Swajger | |
| 5,507,830 A | 4/1996 | DeMane et al. | |
| 5,549,706 A * | 8/1996 | McCarthy | 623/23.28 |
| 5,607,431 A | 3/1997 | Dudasik et al. | |
| 5,704,940 A | 1/1998 | Garosi | |
| 5,713,905 A | 2/1998 | Goble et al. | |
| 5,766,261 A | 6/1998 | Neal et al. | |
| 5,858,020 A | 1/1999 | Johnson et al. | |
| 6,090,146 A | 7/2000 | Rozow, III et al. | |
| 6,126,694 A | 10/2000 | Gray, Jr. | |
| 6,238,435 B1 * | 5/2001 | Meulink et al. | 623/22.12 |
| 6,238,436 B1 | 5/2001 | Lob et al. | |
| 6,330,845 B1 * | 12/2001 | Meulink | 81/462 |
| 6,428,578 B2 * | 8/2002 | White | 623/23.22 |
| 6,676,706 B1 | 1/2004 | Mears et al. | |
| 6,902,583 B2 | 6/2005 | Gerbec et al. | |
| 7,004,972 B2 * | 2/2006 | Yoon | 623/22.4 |
| 2002/0040244 A1 | 4/2002 | Despres, III et al. | |
| 2002/0058999 A1 | 5/2002 | Dwyer et al. | |
| 2002/0059000 A1 | 5/2002 | Dwyer et al. | |
| 2002/0099447 A1 | 7/2002 | Mears et al. | |
| 2002/0116067 A1 | 8/2002 | Mears et al. | |
| 2002/0133234 A1 * | 9/2002 | Sotereanos | 623/23.26 |
| 2002/0151984 A1 | 10/2002 | White | |
| 2003/0130741 A1 | 7/2003 | McMinn | |
| 2003/0149487 A1 | 8/2003 | Doubler et al. | |
| 2003/0204268 A1 * | 10/2003 | Gerbec et al. | 623/23.44 |
| 2003/0220698 A1 * | 11/2003 | Mears et al. | 623/22.4 |
| 2003/0229357 A1 * | 12/2003 | Dye | 606/99 |
| 2004/0243248 A1 * | 12/2004 | Despres et al. | 623/22.42 |
| 2005/0096748 A1 * | 5/2005 | Yoon | 623/22.4 |
| 2005/0125067 A1 * | 6/2005 | Sweeney | 623/19.14 |

OTHER PUBLICATIONS

Matta, "The Anterior Approach for Total Hip Replacement: Background and Operative Technique," HipandPelvis.com [on-line], © 2002-2003 [retrieved Dec. 31, 2003]. Retrieved from the Internet: http://www.hipandpelvis.com/physicians_corner/thr.htm. (2 pages).

Office Action, dated Apr. 1, 2009, in U.S. Appl. No. 11/030,019 (17 pages).

Office Action dated April 14, 2009, in U.S. Appl. No. 10/912,644 (13 pages).

* cited by examiner

METHOD AND INSTRUMENTATION FOR PERFORMING MINIMALLY INVASIVE HIP ARTHROPLASTY

CROSS REFERENCE TO RELATED APPLICATIONS

This application claims the benefit of U.S. Provisional Patent Application No. 60/534,270, filed Jan. 5, 2004, and U.S. patent application Ser. No. 10/912,644, filed Aug. 5, 2004, both of which applications are hereby incorporated by reference, along with the following applications filed on Jan. 5, 2005: U.S. patent application Ser. No. 11/030,020 entitled Method And Instrumentation For Performing Minimally Invasive Hip Arthroplasty and filed in the name of Troy W. Hershberger and Kimberly S. Parcher, and U.S. patent application Ser. No. 11/030,019 entitled Method And Instrumentation For Performing Minimally Invasive Hip Arthroplasty and filed in the name of Troy W. Hershberger.

BACKGROUND OF THE INVENTION

This invention relates to methods and instruments for performing hip arthroplasty, and more particularly to methods for implanting a femoral implant as part of an implantable hip prosthesis.

In one popular method of performing a total hip arthroplasty through two incisions, the femur is prepared by passing instrumentation through a small posterior lateral incision. This posterior incision is similar to the incision made when performing a conventional femoral intramedullary nailing procedure except that the incision is located somewhat more superior. A second, anterior incision is made to facilitate the introduction of instrumentation for preparation of the acetabulum as well as to expose the femur from the anterior side. The surgeon is able to view the femur and resect the femoral head from this anterior side. Access along the femoral axis for reamers and broaches is most readily accomplished, however, through the posterior lateral incision. The surgeon bluntly divides the fibers of the gluteus maximus through the posterior incision to develop a small tunnel through which he may pass the femoral broaches, reamers and, eventually, the femoral implant.

The incision and tunnel must be large enough, of course, to accommodate passage of the full girth of the femoral broach and other instrumentation, and the desired femoral implant. Such a large incision and tunnel can cause damage to the muscle fibers as well as the skin margins by excessive stretching of tissue.

SUMMARY OF THE INVENTION

The present invention provides a novel method employing a two-incision technique to implant a modular hip stem implant into a medullary canal of a patient's femur. In broad terms, the method comprises making a first incision and a separate second incision in the body of the patient, inserting a first portion of the modular hip stem implant through the first incision, inserting a second portion of the modular hip stem implant through the second incision, interconnecting the portions of the hip stem implant in vivo, and driving the modular hip stem implant into the medullary canal.

According to one aspect of the present invention, a novel method of implanting a modular hip stem implant comprises inserting the stem portion of the implant into the medullary canal through a posterior incision, inserting the body portion of the implant through an anterior incision, affixing the body portion onto the stem portion, and driving the hip stem implant into the medullary canal.

According to another aspect of the present invention, a novel method of implanting a modular hip stem implant is provided in which the body portion is inserted through the anterior incision, and the stem portion is inserted through the posterior incision and into a bore in the body portion. The stem portion is retained within the body portion, and the hip stem implant is driven into said medullary canal.

The objects and advantages of the present invention will be more apparent upon reading the following detailed description in conjunction with the accompanying drawings.

DETAILED DESCRIPTION OF THE PREFERRED EMBODIMENTS

Figure 1:
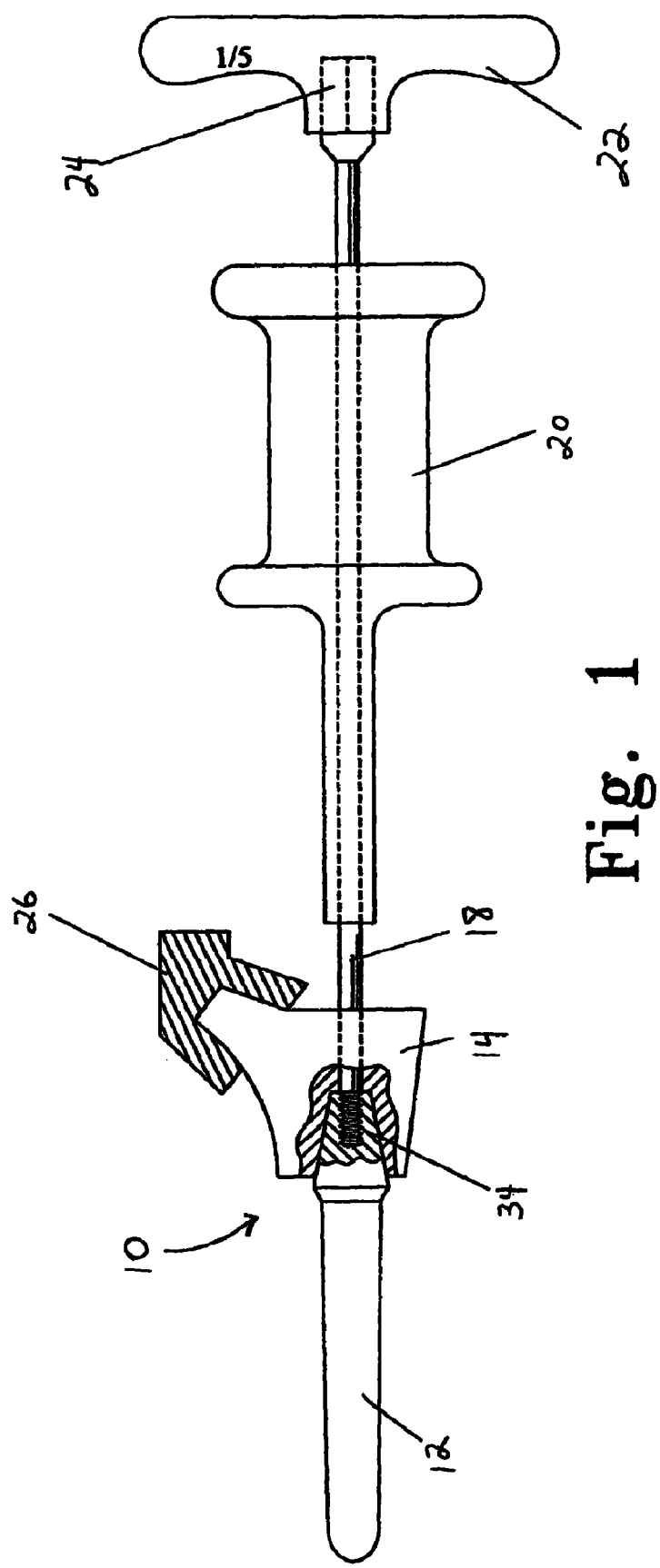
FIG. 1 shows a modular hip stem implant and installation instrumentation.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

It is desired to reduce the size of incisions necessary to perform a total hip arthroplasty in order to minimize trauma to the gluteus muscles and other underlying tissue adjacent the hip joint. One approach to reducing the size of the incisions is to make two smaller incisions having combined size less than the size of an incision typically made in a traditional single-incision hip replacement procedure. According to the present invention, one method of implanting a modular hip stem using a two-incision approach includes placing the stem portion into the medullary canal of the patient's femur through a posterior incision in the body of the patient using an assembly shaft and inserting the body portion through a separate anterior incision in the body, thus reducing the size of the posterior incision necessary to perform the procedure.

A first method according to the present invention uses a hip stem implant design 10, as shown in FIG. 1, generally comprising a stem portion 12, a body portion 14, and a locking screw 16. The hip stem implant 10 is implanted into the femur of the patient using an assembly shaft 18, slap hammer 20, hold back handle 22, lock nut 24 and implant driver 26.

The stem portion 12 has a threaded aperture 34 for receiving the locking screw 16 and securing the body portion 14 to the stem portion 12. The body portion 14 has a bore 28 therethrough for receiving the locking screw 16 into the top of the tapered head 30 of the stem portion 12 and an open cavity 32 for receiving the tapered head 30 of the stem portion 12.

Figure 2:
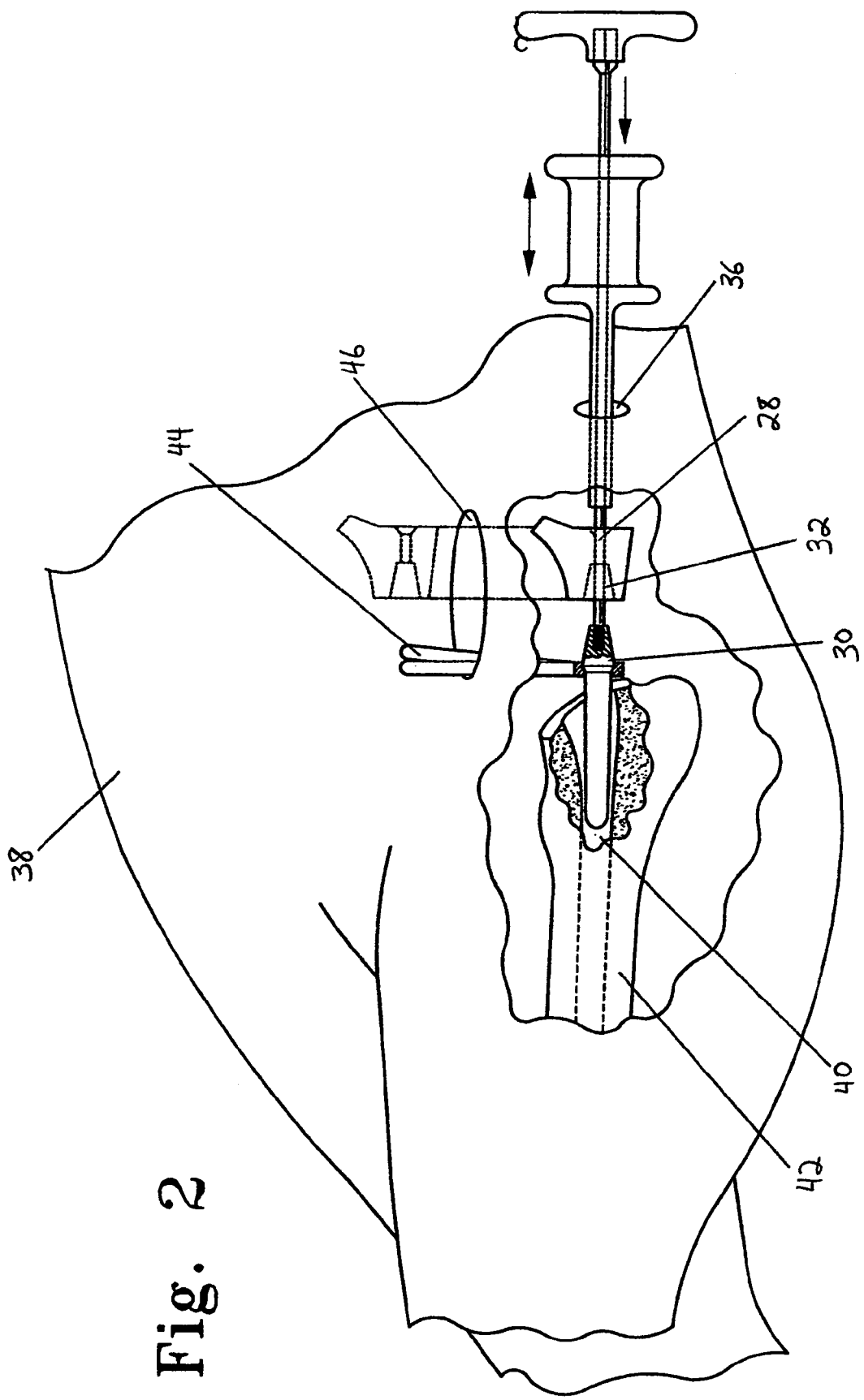
FIG. 2 illustrates a method for implanting the modular hip stem implant of FIG. 1.
Figure 3:
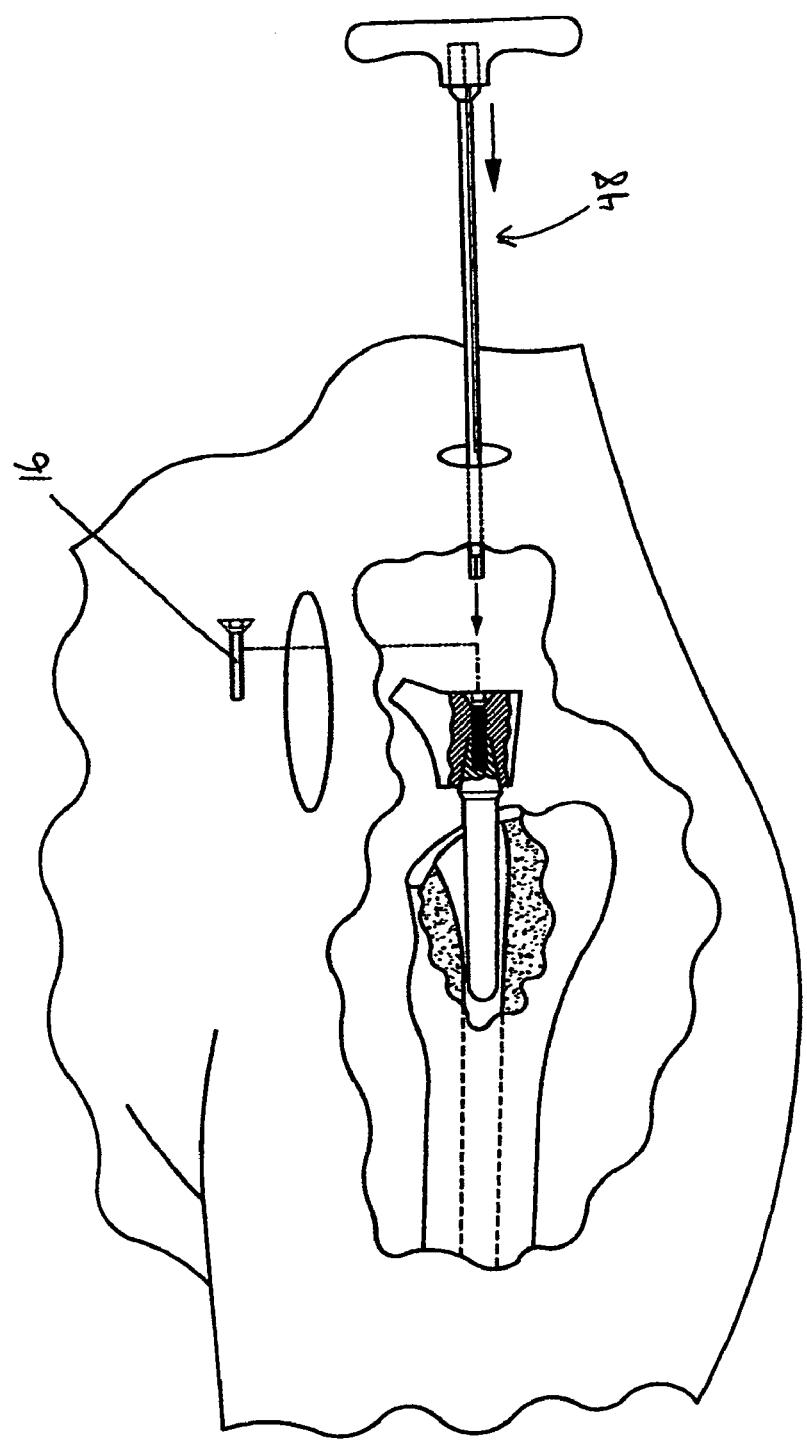
FIG. 3 illustrates implanting of the implant in a patient's medullary canal.

The method illustrated in FIGS. 2 and 3 preferably comprises first inserting the stem portion 12 through a posterior incision 36 in the body of the patient 38 with the assembly shaft 18 and loosely positioning the stem portion 12 into the medullary canal 40 of the patient's femur 42. Forceps 44 are then preferably used to hold the stem portion 12 while the assembly shaft 18 is detached from the stem portion 12. Next, the body portion 14 is preferably inserted through an anterior incision 46 in the body of the patient 36 while the stem portion 12 continues to be held with forceps 44. The assembly shaft 18 is then reattached to the stem portion 12 through the bore 28 of the body portion 14. Next, the slap hammer 20 is slid over the assembly shaft 18 and the hold back handle 22 and lock nut 24 are secured to the end of the assembly shaft 18.

Once situated, the body portion 14 is then impacted onto the stem portion 12 using the slap hammer 20 while preventing the stem portion 12 from seating into the medullary canal 40 by continuing to hold the stem portion 12 with the hold back handle 22. Assembly of the body portion 14 onto the stem portion 12 may be visualized through the anterior incision 46 while impaction of the body portion 14 onto the stem portion 12 is accomplished through the posterior incision 34. The implant driver 26 is then used to hold the body portion 14 while the assembly shaft 18 is detached from the implant 10. Next, the locking screw 16 is preferably inserted through the anterior incision 46 and threaded into the stem portion 12, as shown in FIG. 3, with a screw driver (not shown) manipulated through the posterior incision 36, securing the body portion 14 to the stem portion 12.

Finally, the implant 10 can be seated within the medullary canal 40, as shown in FIG. 3, using a standard punch inserter (not shown) manipulated through the posterior incision 36 and anteversion of the implant 10 guided with the implant driver 26, or by manipulation of the implant driver 26 alone through the anterior incision 46.

Figure 4:
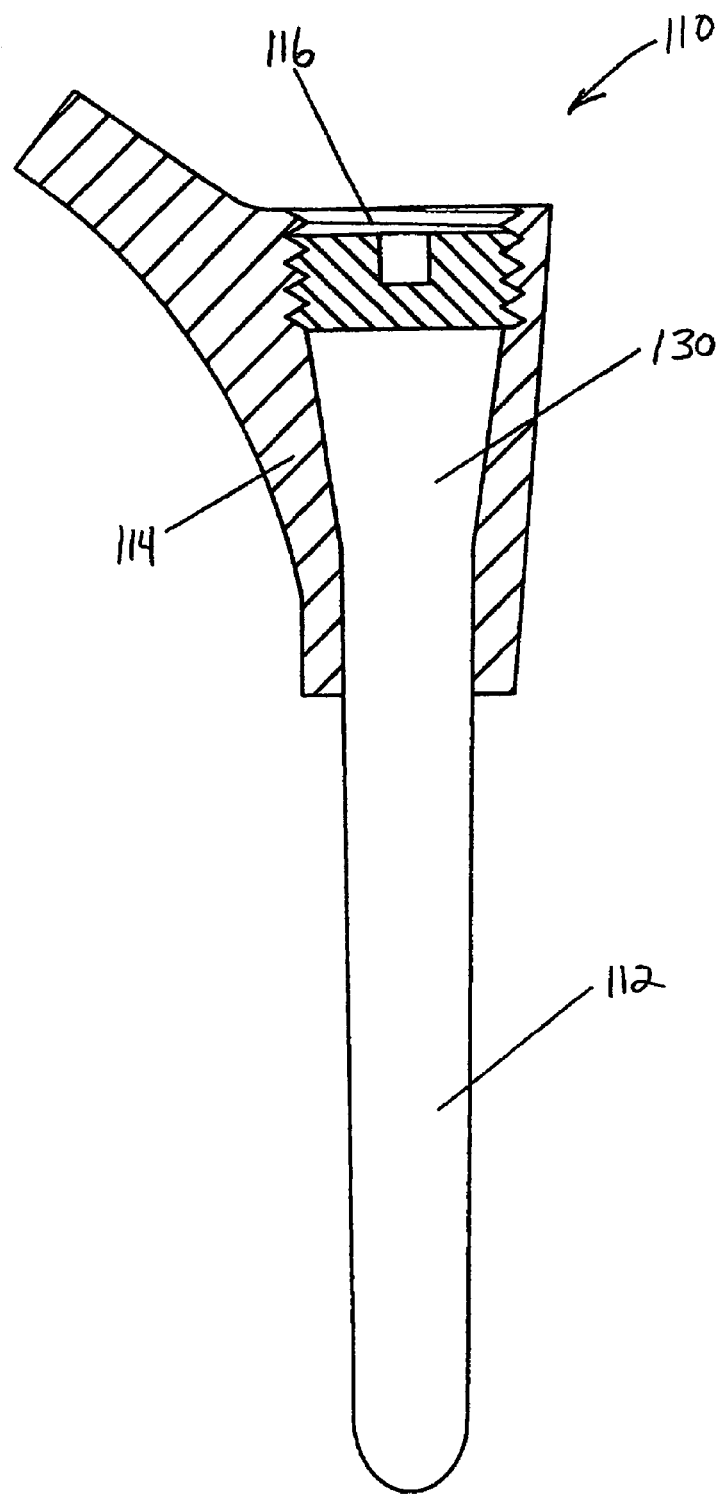
FIG. 4 shows another modular hip stem implant design.
Figure 5:
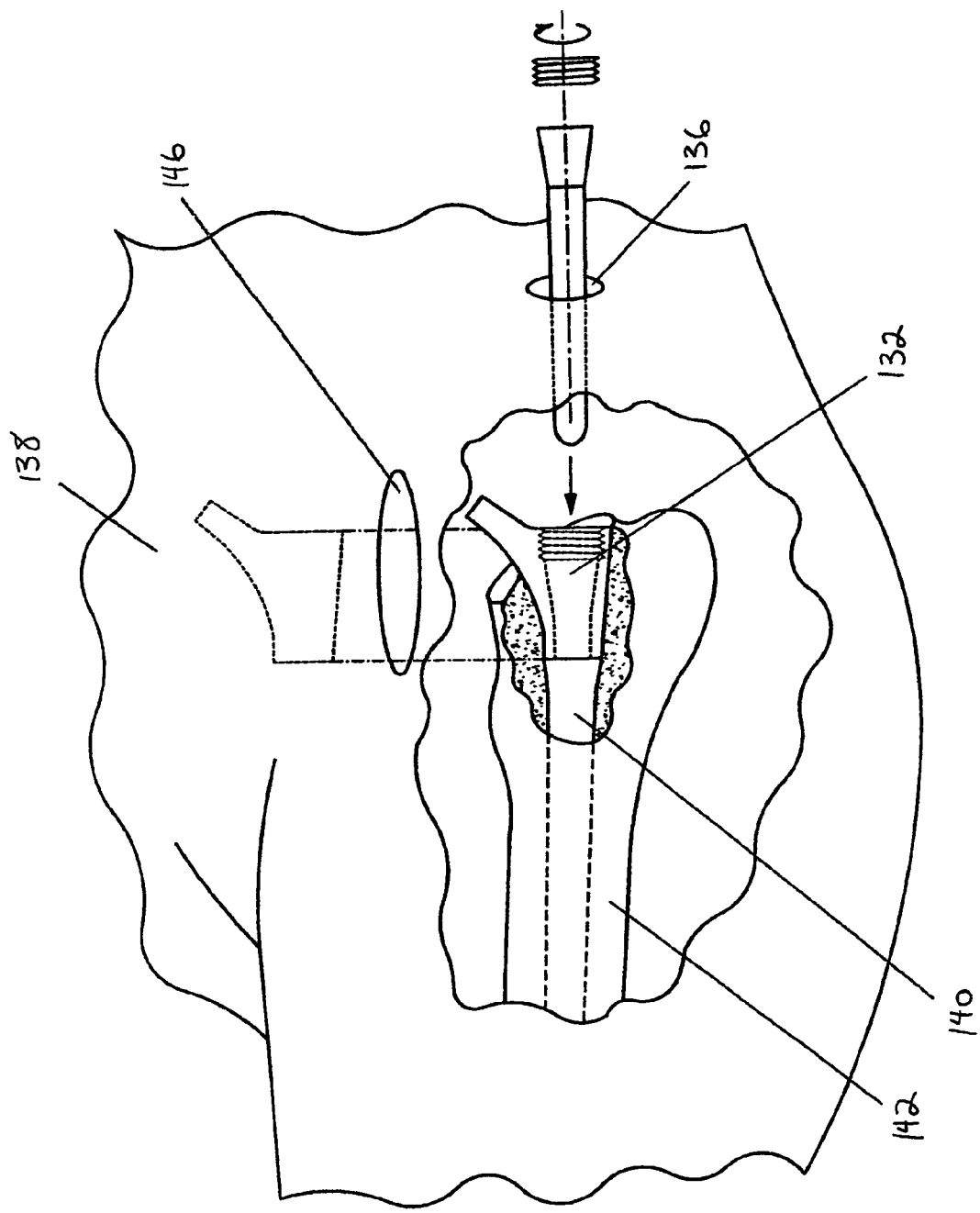
FIG. 5 illustrates another method for implanting the modular hip stem implant of FIG. 4.

Another embodiment of the present invention uses a different hip stem implant design 110 shown in FIGS. 4 and 5, generally comprising a stem portion 112, a body portion and a threaded locking cap 116. The stem portion 112 has a reverse tapered portion 130 enabling the body portion 114 to be inserted through the anterior incision 146, prior to the insertion of the stem portion 112 through the posterior incision 136. The body portion 114 has an open threaded through cavity 132 for receiving the reverse tapered portion 130 of the stem portion 112 and threaded locking cap 116.

The method illustrated in FIG. 5 preferably comprises first inserting the body portion 114 through the anterior incision 146 in the body of the patient 138 and loosely positioning the body portion 114 into the medullary canal 140 of the patient's femur 142. The stem portion 112 is then preferably inserted through the posterior incision 136 with the assembly shaft 118 and advanced through the open threaded through cavity 132 of the body portion 114. Next, the threaded locking cap 116 is inserted through the posterior incision 136 and threaded into the open threaded through cavity 132 of the body portion 114, securing the stem portion 112 within the body portion 114. Finally, the implant 110 can be seated within the medullary canal 140 of the patient's femur 142 by manipulation of the implant driver 126 through the anterior incision 146.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of implanting a modular hip stem implant having a stem portion and a body portion into a medullary canal of a patient's femur, comprising:
   inserting said stem portion into said medullary canal through a posterior incision;
   inserting said body portion through an anterior incision;
   affixing said body portion onto said stem portion, in vivo, by bringing the body and stem portions together along a longitudinal axis of the stem portion; and
   after said affixing, driving said stem portion and said body portion into said medullary canal simultaneously, as a unit.

2. The method of claim 1, wherein said driving includes applying force to an implant driver connected to said body portion, through said anterior incision.

3. The method of claim 1, wherein said driving includes inserting a punch inserter through said posterior incision and applying force to said punch inserter through said posterior incision.

4. A method of implanting a modular hip stem implant having a stem portion and a body portion into a medullary canal of a femur, comprising:
   inserting said body portion into said medullary canal through an anterior incision;
   subsequently inserting said stem portion through a posterior incision and into a bore of said body portion;
   retaining said stem portion within said body portion, in vivo; and
   after said retaining, driving said stem portion and said body portion into said medullary canal simultaneously, as a unit.

5. The method of claim 4, wherein said driving includes applying force to an implant driver connected to said body portion through said anterior incision.

6. A method of implanting a modular hip stem implant into a medullary canal of a patient's femur, comprising:
   making a first incision and a separate second incision;
   inserting a first portion of said modular hip stem implant into the medullary canal through said first incision;
   inserting a second portion of said modular hip stem implant through said second incision;
   interconnecting said first portion and said second portion of said modular hip stem implant within said patient by bringing the first and second portions together along a longitudinal axis of the modular hip stem implant; and
   after said interconnecting, driving said first and second portions of said modular hip stem implant as a unit into said medullary canal.

7. The method of claim 6, wherein said interconnecting includes fastening said first portion to said second portion.

8. The method of claim 7, wherein said driving includes applying force to an implant driver connected to one of said first and second portions through one of said first and second incisions.

9. The method of claim 7, wherein said driving includes inserting a punch inserter through one of said first and second incisions and applying force to said punch inserter through said one of said first and second incisions.

10. The method of claim 6, wherein said interconnecting includes retaining one of said first and second portions within the other portion of said first and second portions.

11. The method of claim 10, wherein said driving includes applying force to an implant driver connected to one of said first and second portions through one of said first and second incisions.

12. The method of claim 10, wherein said driving includes inserting a punch inserter through one of said first and second incisions and applying force to said punch inserter through said one of said first and second incisions.

13. A method of implanting a modular hip stem implant into a medullary canal of a patient's femur, comprising:
   making a first incision and a separate second incision;
   inserting a first portion of said modular hip stem implant into the medullary canal through said first incision;
   inserting a second portion of said modular hip stem implant through said second incision;

interconnecting said first portion and said second portion of said modular hip stem implant within said patient by bringing the first and second portions together along a longitudinal axis of the modular hip stem implant; and simultaneously driving said first portion and said second portion of said modular hip stem implant in a direction substantially parallel with the medullary canal of the patient's femur.

14. The method of claim 13, wherein said interconnecting includes fastening said first portion to said second portion.

15. The method of claim 14, wherein said driving includes applying force to an implant driver connected to one of said first and second portions through one of said first and second incisions.

16. The method of claim 14, wherein said driving includes inserting a punch inserter through one of said first and second incisions and applying force to said punch inserter through said one of said first and second incisions.

* * * * *